(12) United States Patent
Dittrich et al.

(10) Patent No.: US 6,340,365 B2
(45) Date of Patent: *Jan. 22, 2002

(54) DISMOUNTABLE MEDICAL INSTRUMENT WITH A SELF-ORIENTING COUPLING

(75) Inventors: Horst Dittrich, Immendingen; Uwe Bacher, Tuttlingen; Jürgen Rudischhauser, Tuttlingen; Klaus M. Irion, Tuttlingen, all of (DE)

(73) Assignee: Karl Storz GmbH & Co. KG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/230,396
(22) PCT Filed: May 25, 1998
(86) PCT No.: PCT/EP98/03065
   § 371 Date: Apr. 2, 1999
   § 102(e) Date: Apr. 2, 1999
(87) PCT Pub. No.: WO98/53743
   PCT Pub. Date: Dec. 3, 1998

(30) Foreign Application Priority Data

May 27, 1997 (DE) .......................................... 197 22 062

(51) Int. Cl.⁷ .............................................. A61B 17/28
(52) U.S. Cl. ..................................................... 606/205
(58) Field of Search ................................ 606/205, 170, 606/174, 47; 403/325, DIG. 4, DIG. 1; 464/1, 74, 49; 433/126, 127, 128

(56) References Cited

U.S. PATENT DOCUMENTS

| | | | | |
|---|---|---|---|---|
| 5,293,878 A | * | 3/1994 | Bales et al. | 606/205 |
| 5,507,297 A | * | 4/1996 | Slater et al. | 606/205 |
| 5,676,678 A | * | 10/1997 | Schad | 606/170 |
| 5,836,867 A | * | 11/1998 | Speier et al. | 600/112 |
| 5,947,996 A | * | 9/1999 | Logeman et al. | 606/205 |

FOREIGN PATENT DOCUMENTS

| | | | | |
|---|---|---|---|---|
| DE | 38 28 478 A1 | | 5/1989 | |
| DE | G9407278.7 | * | 8/1994 | 606/205 |
| DE | 94 07 278.7 | | 8/1994 | |
| DE | 94 08 931.0 | | 10/1994 | |
| DE | G9408931.0 | * | 10/1994 | 606/205 |
| DE | 94 07 621.9 | | 4/1995 | |
| DE | 197 22 062 A1 | | 12/1998 | |

* cited by examiner

Primary Examiner—David O. Reip
Assistant Examiner—Tan-Uyen T. Ho
(74) Attorney, Agent, or Firm—St. Onge Steward Johnston & Reens LLC

(57) ABSTRACT

A medical instrument has several components and being disassemblable into said several components, one of said components being rotatable with respect to another of said several components by means of a rotary element arranged on said another of said several components. A coupling for a detachable rotationally engaged connection of said one component or to said rotary element is provided, said coupling having two coupling halves engaging into one another along a coupling axis. On each of said coupling halves at least one tooth is arranged, each tooth is disposed at a radial spacing from said coupling axis. Adjacent to each tooth in a circumferential direction at least one gap is provided, into which gap of one coupling half a tooth of the other coupling half enters and fits, and each tooth is equipped in the circumferential direction with a bevel.

17 Claims, 3 Drawing Sheets

DISMOUNTABLE MEDICAL INSTRUMENT WITH A SELF-ORIENTING COUPLING

CROSSREFERENCE OF PENDING APPLICATION

This is a continuation of pending international application PCT/EP98/03065 filed on May 25, 1998.

BACKGROUND OF THE INVENTION

1. Field of the Invention

The present invention relates to a medical instrument that is disassemblable into several components, in particular into a handle and a tubular shaft, one component, in particular the tubular shaft, being rotatable with respect to a further component, in particular the handle, by means of a rotary element arranged on the further component; having a coupling for detachable rotationally engaged connection of the one component to the rotary element of the further component, the coupling having two coupling halves which engage into one another along a coupling axis.

2. Related Prior Art

A medical instrument of this kind is marketed by the company styled Karl Storz GmbH & Co.

Medical instruments that are disassemblable into several components are widely used in surgery. Instruments suitable for minimally invasive surgery are configured as tubular shaft instruments which have a proximal handle and a tubular shaft. A working insert, which has at its distal end, for example, spatulas, needles, electrodes, loops, mouth parts functioning as scissors or forceps, and the like, is guided through the tubular shaft.

Disassembly of the instruments into handle, tubular shaft, and working insert allows optimum cleaning, as well as flexible utilization of the instrument by combining different components with one another.

Connection of the components must, however, proceed easily and quickly, so as to allow components to be exchanged, possibly even during the operation, without disrupting the proper execution of the operation.

One difficulty in connecting the components, usually a handle to a tubular shaft containing the working insert, arises from the fact that it is desirable for the tubular shaft to be connected rotatably about its longitudinal axis to the handle. The reason is that mouth parts can then be brought into any desired rotational position with respect to the handle, so that the surgeon can establish the most favorable relative rotational position between handle and mouth parts.

One known detachable rotationally engaged connection between handle and tubular shafts is accomplished by a coupling in which a polygonal member is provided.

In instruments of the Storz company, the coupling comprises an externally hexagonal member which engages in tight-fitting and positive and thus rotationally engaged fashion into an internally hexagonal member of female configuration on the coupling half of the handle. The female half of the coupling is connected to a rotary element so that the tubular shaft can rotate relative to the handle via the rotary element.

When connecting the two coupling halves, however, the problem arises that introduction of the polygonal member into the female shape by simple sliding or insertion into one another is not possible in every rotational position of the coupling halves, but rather is possible only if the externally hexagonal member is exactly in alignment with the internally hexagonal member. If such is not the case, the coupling halves must be rotated until they are exactly in alignment. This is cumbersome, complicates the process of closing the coupling, and requires close attention.

It is therefore the object of the invention to create a medical instrument that is disassemblable into several components, in which connection of the components can be performed quickly and easily and without close attention.

SUMMARY OF THE INVENTION

According to the present invention, the object is achieved, in an instrument of the kind cited initially, in that there is arranged on each coupling half, at a radial spacing from the coupling axis, at least one tooth adjacent to which in the circumferential direction is at least one gap into which a tooth of the other coupling half can enter and fit; and that each tooth is equipped in the circumferential direction with a bevel.

This yields a self-orienting coupling in which the two coupling halves are constrainedly guided by the beveled teeth while being connected. The need for a rotary motion to be performed consciously by the person fitting the two components together, in order to fit the two coupling halves into one another, is thus eliminated.

The reason is that because teeth with a bevel are provided, the coupling halves are deflected, as they are axially fitted together and encounter one another, regardless of their position, in such a way that the teeth slide past one another and are involuntarily introduced into adjacent gaps. The person fitting together the components therefore does not need to ensure that the coupling halves are correctly oriented; this is a decisive advantage, especially when components are being exchanged during an operation. The process of fitting together the coupling halves and thus the components proceeds particularly quickly, and requires neither concentration nor attention on the part of the person fitting the components together.

In an embodiment of the invention, each tooth is equipped with a bevel on either side of a tip.

The advantage of this feature is that the teeth are deflected in one or the opposite circumferential direction depending on how they encounter one another, and the teeth can enter into the gaps in aligned fashion after a relatively short rotational movement. In the case of teeth having only one bevel, deflection always occurs only in one circumferential direction.

In a further embodiment, two teeth are provided on each coupling half.

This feature has the advantage of ensuring secure meshing of the coupling halves with a relatively small rotation angle.

In a particularly preferred embodiment, two teeth are provided on one coupling half, and four teeth on the second coupling half.

This has the advantage of ensuring that two teeth encounter each other in every case, thus making possible secure meshing. The stress on the four teeth is minimized, so that the four teeth wear away less quickly and the service life of the coupling is increased. This makes it possible to arrange the four teeth on the instrument half which is more valuable or which is intended to have a longer service life.

In a further embodiment, the bevels of the teeth are at an acute angle to one another.

This embodiment offers the advantage of ensuring, because of the relatively sharply inclined contact surfaces, that the coupling halves are guided securely into one another with a relatively long axial coupling travel and a relatively small relative rotation of the coupling halves.

In the case of a tooth with only one bevel, the tip is located approximately on the extension of one tooth flank, and thus constitutes the acute angle.

In a further embodiment, the bevels of the teeth are at an oblique angle to one another.

This feature allows teeth with a low overall height.

In a particularly preferred embodiment, the bevels of the teeth are at an angle of approximately 90 degrees to one another.

This geometry offers the advantage of a low overall height while at the same time allowing the coupling halves to be guided securely into one another.

In a further preferred embodiment, the tips of the teeth have sharp edges.

The advantage here is to ensure, even if two tips encounter one another diametrically, that they slide immediately in one direction or another, and thus that the teeth are introduced into the corresponding gaps.

In a further embodiment, the tips of the teeth are rounded.

The advantage of this feature is that the teeth are more resistant to wear phenomena when the tips encounter one another directly.

In a further embodiment of the invention, the bevels of the teeth are curved outward in profile.

The advantage of this feature is that two teeth which encounter one another at their bevels as the coupling halves are being inserted into one another are essentially in only point contact during the rotational movement caused as the teeth encounter each other, and the rotation operation therefore proceeds with very little friction.

In a further embodiment of the invention, the teeth have magnetic tips, the magnetic tips of the one coupling half being opposite in polarity to the magnetic tips of the other coupling half.

The feature has the advantage that if the tips happen to be exactly aligned with one another, the opposite polarities of the tips ensure that because of the repulsive forces, they are deflected in one direction or the other even before meeting, so that the self-orienting or self-aligning operation proceeds particularly reliably and gently, thus helping to reduce material wear especially in the case of very slender instruments.

In a further embodiment, the teeth of one coupling half are joined to one another circumferentially via material bridges, and the material bridges have radially set-back recesses into which the teeth of the other coupling half engage in such a way that the two coupling halves are inhibited in terms of axial separation.

The advantageous aspect of this feature is that the two closed coupling halves can slide apart axially only after overcoming a resistance.

In a preferred embodiment, the two components are locked in terms of axial separation by an interlock that is separate from the coupling.

The advantage here is that the interlock can be arranged anywhere within the region in which the two components engage into one another. This moreover makes possible a particularly simple configuration, for example in the form of a snap groove on one component and a snap lug on the other component.

In a further embodiment of the invention, in a tubular shaft instrument four teeth are configured on the exterior of the tubular shaft, and at an axial spacing therefrom an annular groove of the interlock is cut in; and two diametrically opposite teeth are provided on the inner side of the rotary element on the handle, a locking element which engages inhibitingly into the annular groove being provided on the handle.

The four teeth on the exterior of the tubular shaft are provided at points which are favorably located for machining; the teeth can be machined out from a solid material. It is equally simple to recess the annular groove into the exterior of the tubular shaft.

All that is necessary is to cut out the two diametrically opposite teeth from the inner side of the rotary element. The locking element which engages into the annular groove in order to bring about axial inhibition can be provided on the handle in a user-friendly arrangement. This is easy in terms of production engineering, and easy to manipulate.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

The invention will be explained and described in more detail below with reference to a selected exemplifying embodiment in conjunction with the appended drawings, in which.

DETAILED DESCRIPTION OF A PREFERRED EMBODIMENT

Figure 1:
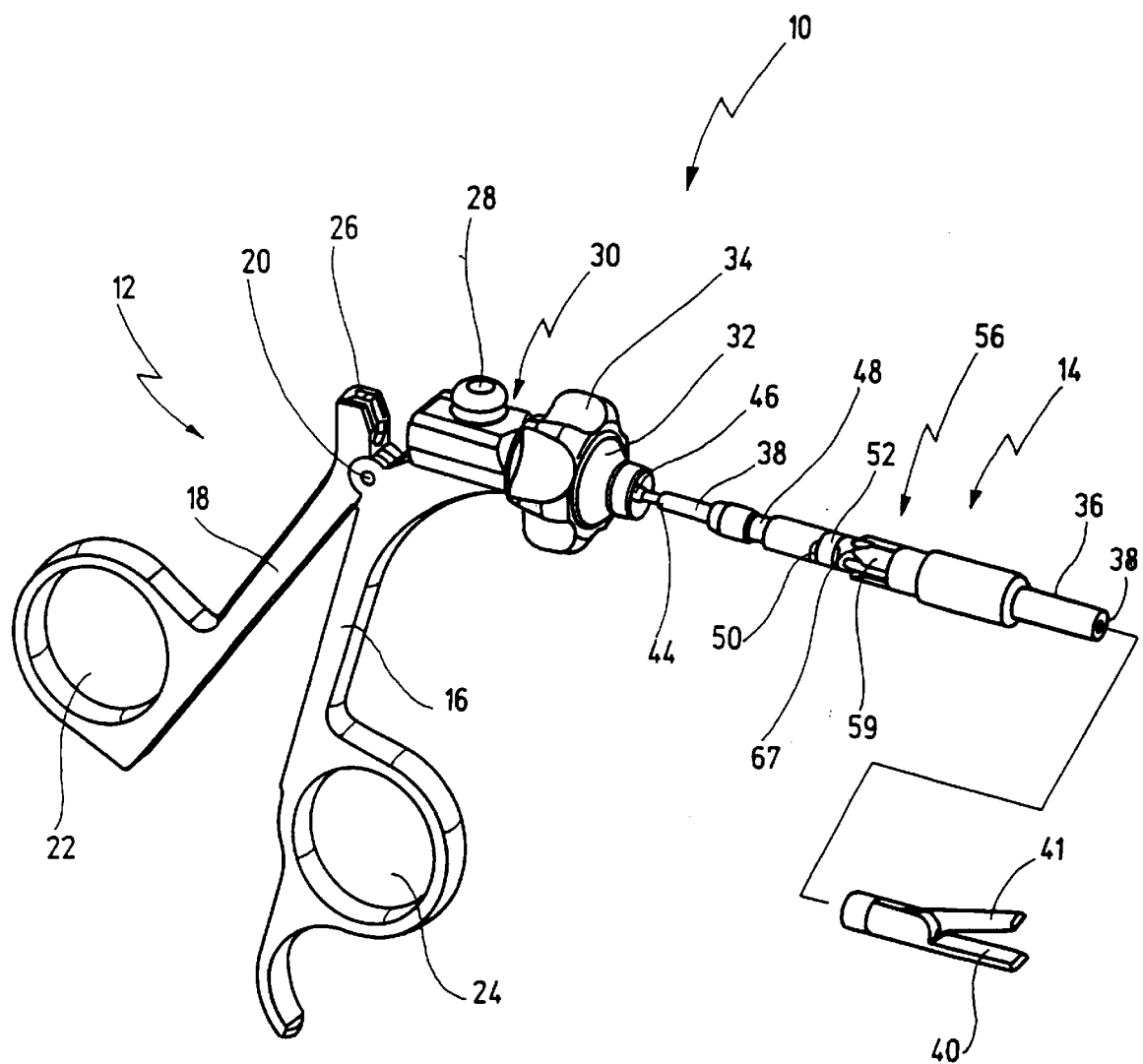
FIG. 1 shows a perspective exploded view of a disassemblable medical instrument.
Figure 2:
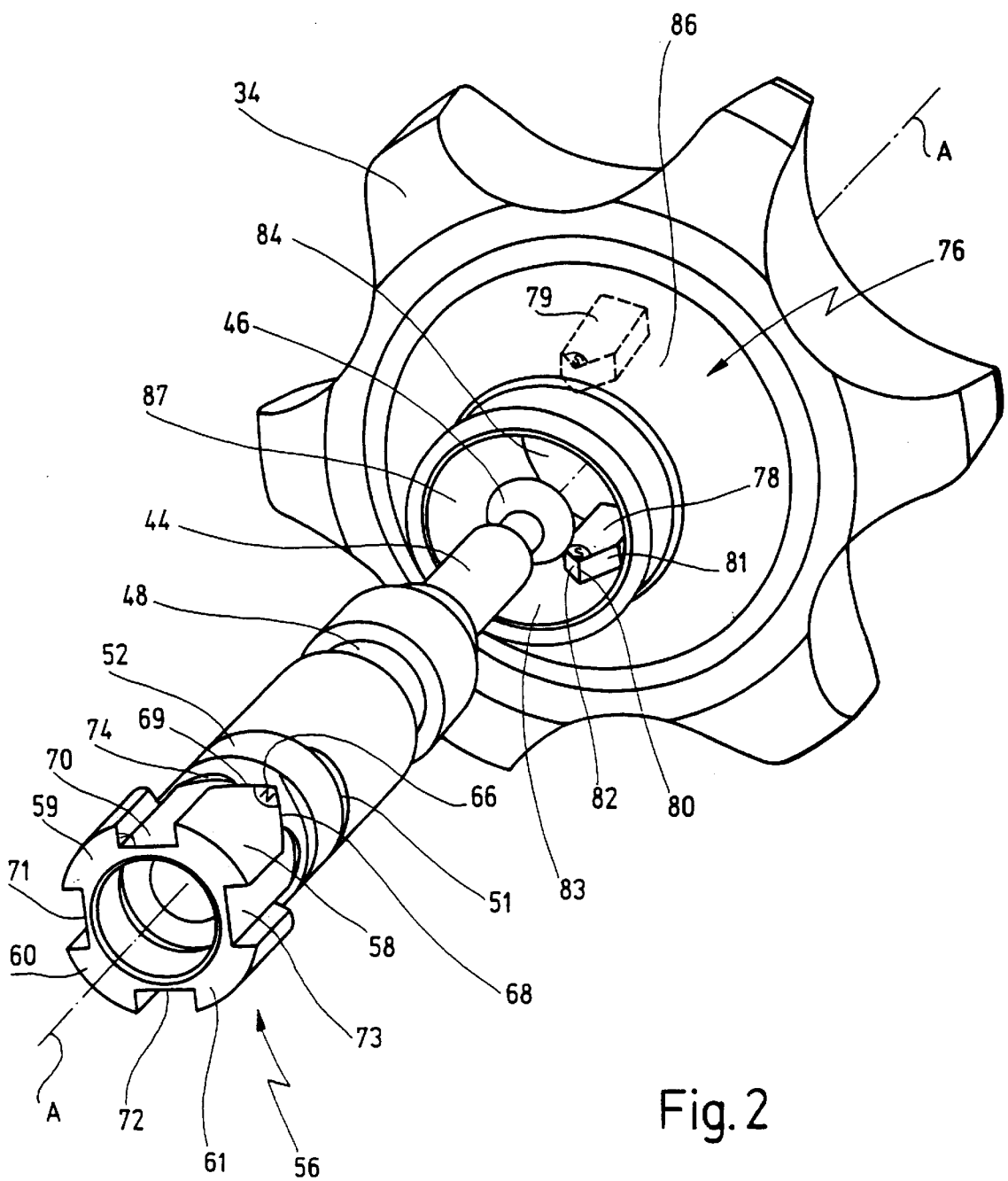
FIG. 2 shows a greatly enlarged partial representation of the constituents which carry the two coupling halves of the coupling.
Figure 3:
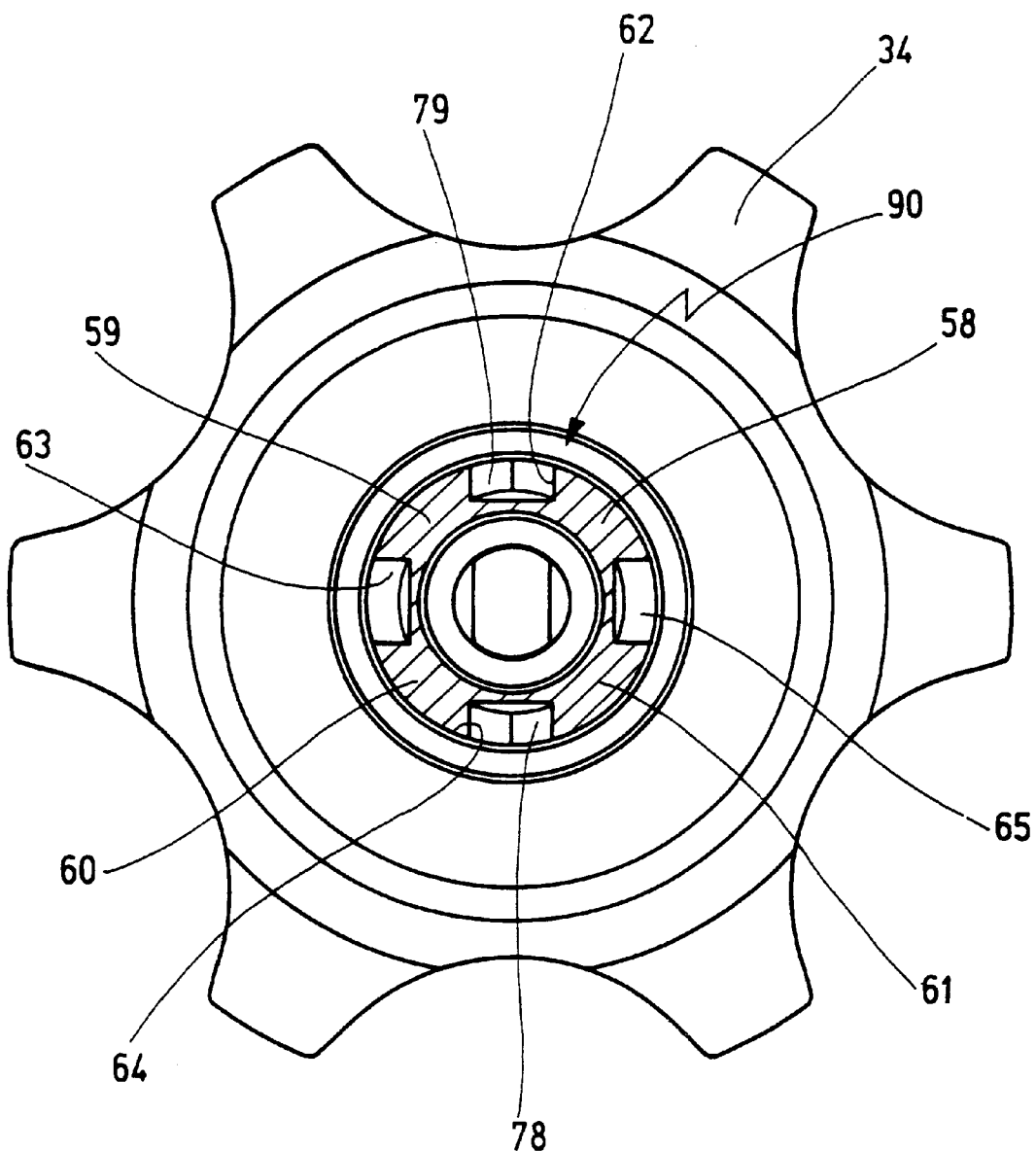
FIG. 3 shows a cross section through a coupling element with the coupling closed.

A disassemblable medical instrument shown in FIGS. 1 through 3 is labeled in its entirety with the reference character 10.

Instrument 10 has as one component a handle 12, and as a further component a tubular shaft 14 detachably connectable thereto.

Handle 12 has a fixed grip element 16 to which a movable grip element 18 is pivotably attached via a hinge 20.

The two grip elements 16 and 18 have at their outer ends finger loops 22 and 24, respectively.

A socket 26 whose nature and purpose will be described later is cut out at the upper end of movable grip element 18.

A locking knob 28 of an interlock 30 is arranged at the upper end of fixed grip element 16.

A rotary element 32 in the form of an adjusting wheel 34 is arranged at the distal end of fixed grip element 16 facing toward the proximal end of tubular shaft 14. Adjusting wheel 34 is attached rotatably.

Tubular shaft 14 has a tube 36 in whose inner side a rod-shaped

Actuation element 38 projects distally beyond tube 36 and carries two mouth parts 40 and 42.

Actuation element 38 projects proximally beyond tube 36 in a segment 44, and carries at its external proximal end a ball 46.

Ball 46 is provided in order to be received in socket 26 of movable grip element 18.

For that purpose, as indicated in FIG. 1, tubular shaft 14 along with actuation element 38 is pushed through a continuous opening in fixed grip element 16 which also passes centeredly through adjusting wheel 34, until ball 46 comes to rest in socket 26. This can occur in a specific pivoted position of movable grip element 18. When movable grip element 18 is moved out of that position, the pivot movement is converted via the ball-and-socket joint into a linear displacement movement of actuation element 38, which in turn opens or closes mouth parts 40, 42 by way of that linear movement.

A first coupling half 56 is arranged on the exterior of the proximal end of tube 36.

As is particularly evident from the perspective view of FIG. 2, coupling half 56 has four teeth 58, 59, 60, 61 each offset circumferentially by 90 degrees. Adjacent to each tooth in the circumferential direction is a respective gap 62, 63, 64, 65. The circumferential width of each tooth 58, 59, 60, 61 is equal to the circumferential width of a gap 62, 63, 64, 65.

Each tooth has a tip facing handle 12; tip 66 of tooth 58 is visible in FIG. 2, and tip 67 of tooth 59 in FIG. 1.

A bevel is present on either side of each tip of a tooth: bevels 68 and 69 of tooth 58 are visible in FIG. 2 on either side of tip 66. The bevels thus extend in a circumferential direction, and are inclined, when viewed from a radial plane at the level of tip 66, from the proximal to the distal end of shaft 14. The bevels enclose an angle of approximately 90 degrees.

As is evident from the perspective representation of FIG. 2, the four teeth 58, 59, 60, 61 are joined in the circumferential direction via material bridges (not designated here in further detail) in which flat recesses 70, 71, 72, and 73, slightly set back radially, are present.

The circular outer contour of the shaft or of tube 36 thus transitions in each case via a ramp (ramp 74 of recess 70 is visible in FIG. 2) into a recess.

A second coupling half 76 is arranged on adjusting wheel 34 of fixed grip element 16.

Second coupling half 76 has two diametrically opposite teeth 78 and 79 which each have a tip (tip 80 of tooth 78 is visible in FIG. 2).

Each tip is equipped on each side with a bevel 81 and 82.

The two teeth 78 and 79 are arranged on an inner side 83 of a centered continuous opening 84 in adjusting wheel 34.

The contour of teeth 78 and 79 with respect to the tip and to bevels 81 and 82 is identical to the contour of teeth 58, 59, 60, and 61 of first coupling half 56, although the tips 80 of teeth 78, 79 are located opposite the tips of teeth 58, 59, 60, 61. Viewed in a circumferential direction, gaps 86 and 87 exist between the two diametrically opposing teeth 78 and 79.

As is evident in particular from FIG. 2, teeth 58 through 61 of first coupling half 56 are equipped in the region of their tips 63 through 66 with a magnetic insert (symbol N).

Teeth 78 and 79 of second coupling half 76 are also correspondingly equipped in the region of their tips with magnetic inserts, but of opposite polarity to those of the teeth of coupling half 56 (symbol S).

The two coupling halves 56 and 76, considered together, constitute a coupling 90.

To close coupling 90, tubular shaft 14, as shown in FIGS. 1 and 2, is inserted into central opening 84 of adjusting wheel 34 or handle 12. If the two teeth 78 and 79 of second coupling half 76 directly encounter two diametrically opposite gaps 62 and 64, as shown in FIG. 3, the two constituents (tubular shaft 14 and handle 12) can be inserted into one another without relative rotation. This is exactly possible only in two relative positions offset 90 degrees from one another.

In all other relative rotational positions, bevels 81, 82 of teeth 78 and 79 encounter corresponding bevels of two of the four teeth 58, 59, 60, and 61, which then results in a constrainedly guided relative rotation of the two elements about coupling axis A, until an alignment exists such that the two diametrically opposing teeth 78, 79 can enter into correspondingly diametrically opposite gaps in first coupling half 56. Coupling 90 is thus self-orienting or self-aligning.

Initiation of the rotating movement as the teeth approach one another is further assisted by the repulsive forces of the magnetic tips of opposite polarity. If the coupling happens to be put in place in such a way that tip 66 of tooth 58 exactly meets the tip of tooth 79, even before the two tips mechanically encounter one another the repulsive force of the poles produces a clockwise or counterclockwise rotation about coupling axis A, thus preventing the tips from striking one another directly. The repulsive forces then also assist further rotary movement in the rotation direction once it has begun.

The arrangement of the two teeth 78, 79 is such that they slide with gentle radial pressure over the exterior of shaft 14, and then mesh via the ramps (only ramp 74 is shown in FIG. 2) into the slightly radially set-back recesses 70 and 72.

Ramp 74, and then the corresponding opposite ramp 100, already ensure a certain interlocking of the two teeth 78 and 79 in terms of axial withdrawal.

The actual interlocking in terms of axial withdrawal is accomplished via interlock 30, i.e. interlock knob 28 engages into annular groove 48.

Once teeth 78 and 79 of the one coupling half 76 have engaged into the corresponding gaps of the other coupling half 56, a positive and thus also rotationally engaged connection has been created between adjusting wheel 34 and tubular shaft 14.

In the assembled state, adjusting wheel 34 can therefore be used to rotate tubular shaft 14, together with actuation element 38 received therein, about coupling axis A relative to handle 12, so that mouth parts 40 and 42 can be brought into a relative rotational position with respect to handle 12 that is favorable for the operator. The provision of the ball-and-socket joint makes this rotation possible in any pivoted position of movable grip element 18.

To ensure that no relative rotation occurs between actuation element 38 and tubular shaft 14, actuation element 38 is flattened in the region of two clamping pieces 50, 51. Clamping pieces 50, 51 engage into the flattened area and are held by a retaining ring 52. As a result, axial displacement of actuation element 38 in tube 36 is possible, but rotation of actuation element 38 relative to tube 36 is not possible.

To release coupling 90, locking knob 28 must be actuated so that its locking element (not shown here) emerges from annular groove 48; tubular shaft 14 can then be withdrawn, a certain amount of force being necessary to move the two teeth 78 and 79 over ramps 74 of the corresponding recesses.

This ensures that when locking knob 28 released, tubular shaft 14 does not fall off handle 12 in the event of careless handling.

What is claimed is:

1. A medical instrument having several disassemblable components, one of said several components being rotatable with respect to another one of said several components by means of a rotary element arranged on said another one of said several components, and a coupling for a detachable rotationally engaged connection of said one of said several components to said rotary element, said coupling having two coupling halves engaging into one another along a coupling axis, at least one tooth being arranged on one of said halves, at least a pair of radially spaced apart teeth being arranged on the other of said coupling halves and defining therebetween a recess having a radially set back bottom, said bottom and said one tooth being formed with first and second surfaces, respectively, said first and second surfaces extending angularly with respect to the coupling axis and complementary to one another as the recess receives the one tooth upon axial displacement of the halves relative each other and wherein each tooth is equipped in the circumferential direction with a bevel.

2. The medical instrument of claim 1, wherein each tooth is equipped with a bevel on either side of a tip of said tooth.

3. The medical instrument of claim 1, wherein two teeth are provided on each of said coupling halves.

4. The medical instrument of claim 1, wherein four teeth are provided on one coupling half, and two teeth are provided on the other coupling half.

5. The medical instrument of claim 1, wherein each tooth is equipped with a bevel on either side of a tip, and wherein said bevels of said tooth are at an acute angle to one another.

6. The medical instrument of claim 1, wherein each tooth is equipped with a bevel on either side of a tip, and wherein said bevels of said tooth are at an oblique angle to one another.

7. The medical instrument of claim 1, wherein each tooth is equipped with a bevel on either side of a tip, and wherein said bevels of said tooth are at an angle of approximately 90 degrees to one another.

8. The medical instrument of claim 1, wherein said tooth has a tip, said tip of said tooth has a sharp edge.

9. The medical instrument of claim 1, wherein said tooth has a tip, said tip of said tooth is rounded.

10. The medical instrument of claim 1, wherein said bevel of said tooth has a curved outward in profile.

11. The medical instrument of claim 1, wherein said tooth has a magnetic tip, the magnetic tip of a tooth of one coupling half being opposite in polarity to a magnetic tip of a tooth of the other coupling half.

12. The medical instrument of claim 1, wherein said components are locked in terms of axial separation by an interlock that is separate from said coupling.

13. The medical instrument of claim 1, having a handle and a tubular shaft, said tubular shaft being rotatable with respect to said handle, and wherein said rotary element is arranged on said handle.

14. The medical instrument of claim 12, having a handle and a tubular shaft, said tubular shaft being rotatable with respect to said handle, and wherein said rotary element is arranged on said handle, and wherein four teeth are configured on an exterior of said tubular shaft, at an axial spacing therefrom an annular groove of said interlock is cut in, and two diametrically opposite teeth are provided on an inner side of said rotary element on said handle, and a locking element which engages inhibitingly into said annular groove is provided on said handle.

15. A medical instrument having several disassemblable components, one of said several components being rotatable with respect to another one of said several components by means of a rotary element arranged on said another one of said several components, and a coupling for a detachable rotationally engaged connection of said one of said several components to said rotary element, said coupling having two coupling halves engaging into one another along a coupling axis, two teeth arranged on each of said coupling halves, each tooth disposed at a radial spacing from said coupling axis, at least one gap is provided adjacent to each tooth in a circumferential direction on one of said halves, said gap having a bottom, which extends parallel to the coupling axis, and a ramp, which extends angularly from the bottom toward the other half and is sized such that a tooth of the other coupling half can enter and fit, and wherein each tooth is equipped in the circumferential direction with a bevel, each of the teeth on the other half having an inclined surface which extends complementary to the ramp as the halves move axially toward one another.

16. The medical instrument of claim 15, wherein each tooth is equipped with a bevel on either side of a tip of said tooth.

17. The medical instrument of claim 15, wherein said tooth has a tip, said tip of said tooth has a sharp edge.

* * * * *

UNITED STATES PATENT AND TRADEMARK OFFICE
CERTIFICATE OF CORRECTION

PATENT NO.    : 6,340,365 B2
DATED         : January 22, 2002
INVENTOR(S)   : Horst Dittrich et al.

It is certified that error appears in the above-identified patent and that said Letters Patent is hereby corrected as shown below:

<u>Column 4,</u>
Line 38, please insert -- Fig. 4 shows the ramp and corresponding opposite ramp in an interlocking relationship. --

Signed and Sealed this

Third Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.    : 6,340,365 B2
DATED         : January 22, 2002
INVENTOR(S)   : Horst Dittrich et al.

It is certified that error appears in the above-identified patent and that said Letters Patent is hereby corrected as shown below:

<u>Title page,</u>
Item [73], Assignee, should read -- Karl Storz GmbH & Co. KG --

Signed and Sealed this

Eighteenth Day of March, 2003

JAMES E. ROGAN
*Director of the United States Patent and Trademark Office*